United States Patent [19]

Karell

[11] Patent Number: 5,759,198

[45] Date of Patent: Jun. 2, 1998

[54] METHOD AND APPARATUS FOR TREATING AND PREVENTING LEG CRAMPS AND OTHER MUSCLE CONTRACTIONS AND SLEEP DISORDERS

[76] Inventor: Manuel L. Karell, 3573-22 St., San Francisco, Calif. 94114

[21] Appl. No.: 753,777

[22] Filed: Dec. 2, 1996

Related U.S. Application Data

[60] Provisional application No. 60/008,205, Dec. 5, 1995.

[51] Int. Cl.$^6$ .................................................. A61N 1/18
[52] U.S. Cl. ........................ 607/48; 607/46; 607/63
[58] Field of Search ........................ 607/46, 48, 49, 607/63, 64

[56] References Cited

U.S. PATENT DOCUMENTS

| | | | |
|---|---|---|---|
| 4,757,453 | 7/1988 | Nasiff | 364/415 |
| 4,817,628 | 4/1989 | Zealear | 128/741 |
| 5,133,354 | 7/1992 | Kallok | 607/48 |
| 5,284,161 | 2/1994 | Karell | 128/848 |
| 5,331,851 | 7/1994 | Parviainen | 73/379 |
| 5,562,718 | 10/1996 | Palermo | 607/46 |
| 5,571,144 | 11/1996 | Schroeppel | 607/28 |
| 5,571,205 | 11/1996 | James | 623/24 |
| 5,578,065 | 11/1996 | Hattori et al. | 607/46 |

*Primary Examiner*—George Manuel
*Assistant Examiner*—Carl H. Layno

[57] ABSTRACT

Method and Apparatus for Treating and Preventing Leg Cramps and other Muscle Contractions and Sleep Disorders (EX-Cramp™—a device for relieving cramping muscles) is a medical device using the physiologic principle that volitional muscles are placed in opposition for a desired movement to occur: while a muscle contracts, its physiologically opposing muscle must relax. The EX-Cramp™—a device for relieving cramping muscles, monitors a muscle that inappropriately contracts and cramps, and before the cramp occurs, stimulates the physiologically opposing muscle, thereby relaxing and relieving cramping.

15 Claims, 4 Drawing Sheets

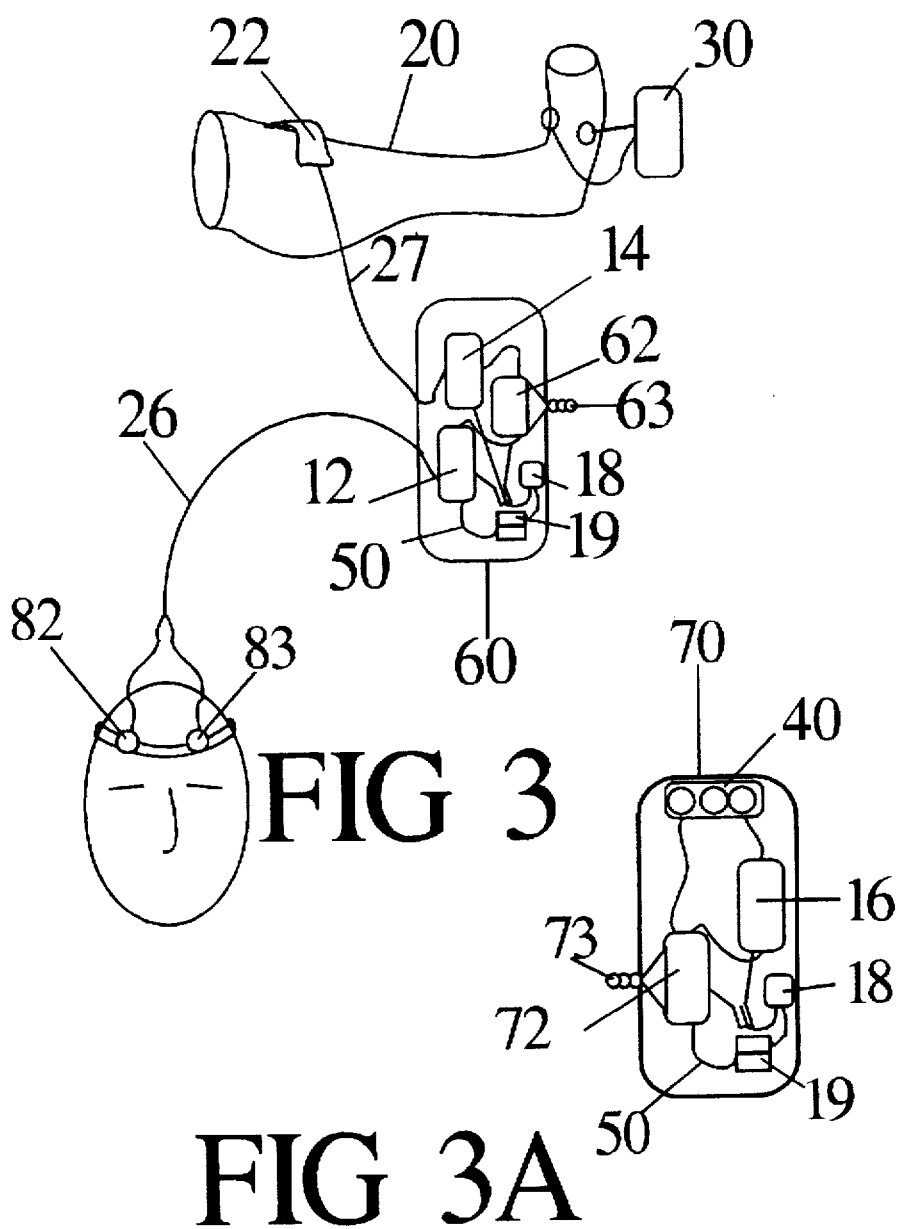

METHOD AND APPARATUS FOR TREATING AND PREVENTING LEG CRAMPS AND OTHER MUSCLE CONTRACTIONS AND SLEEP DISORDERS

BACKGROUND

1. Field of invention

The following is a continuation for provisional patent application Ser. No. 60/008205 filed Dec. 5, 1995.

This apparatus pertains to medical devices and methods for evaluating and controlling muscle function, in particular, to a method and apparatus for relieving night leg muscle cramping and other muscle contraction/cramping and sleep disorders.

2. Description of Prior Art

Monitoring, stimulating, and telemetry thereof of muscles, are well known in medicine. There are many known beneficial uses for a pulse from an electrical pulse generator to cause depolarization of muscle cells and a consequent muscle contraction of the muscle. For example, U.S. Pat. No. 5571144 to Schroeppel, 1996, teaches how a cardiac pacer monitors the heart tone and chronicity to provide a cardiac stimulator that adjusts the pulse energy automatically and dynamically in response to changes in the capture threshold. Another example of a pulse generator is U.S. Pat. No. 5571205, to James, 1996, which teaches how monitoring and pulsing are used in artificial limbs in amputees; patterns are monitored from step to step, and computer software determine the state of muscle flexion/extension thereby initiating appropriate stimulative changes to assist in walking. Another use of monitoring and pulse generation is that found in U.S. Pat. No. 5,284,161 to Karell, 1994 in which soft palate muscles are stimulated to prevent or abort snoring and sleep apnea. U.S. Pat. No. 5331851, issued to Parviainen, 1994, teaches a method for measuring muscular functionality by measuring the working condition of muscles utilizing integrated systems including mechanical devices for straining muscles, measuring equipment, and data processing/recording equipment. U.S. Pat. No. 4817628 to Zealear, 1989, teaches yet another method for monitoring and stimulating nerves and muscles for the purpose of evaluating disease and for making treatment decisions. U.S. Pat. No. 4757453 to Nasiff, 1988, teaches monitoring using piezoelectric transducers for biomedical data processing in which a piezoelectric material converts a mechanical movement into an electrical signal.

Arranged for a specific function in the animal body, volitional muscles are set physiologically in opposition to each other. Thus in order to have a desired movement, one muscle will contract while the physiologically opposing muscle will relax. For example, to bend an arm, the biceps muscle contracts; but in order for the arm to bend, the opposing triceps muscle must relax. If both muscles were to contract at the same time, the desired movement would not occur.

Night leg cramps (a very painful condition) and the Restless Leg Syndrome (a sleep disorder) are common disorders which cause many awakenings during the night resulting in excessive daytime sleepiness and fatigue. The resultant morbidity may cause hardship, such as cognitive problems, sexual dysfunction, hypertension, economic loss, or even loss of life, for example, by falling asleep at the wheel resulting in automobile accidents. Also, muscle cramping during sport activities are well known to occur.

Various medications, such a quinine sulfate, have been used for years; however, research has not shown any medication as reliably effective. Likewise, although certain exercising programs claim to be effective for eliminating muscle cramping and night leg cramps, research again failed to confirm this theory.

A method and apparatus that could prevent night leg cramps and other muscle contracting disorders will be beneficial. A method and apparatus that could abort muscle cramps and other muscle contracting disorders will be beneficial. The present invention accomplishes these goals.

SUMMARY OF THE INVENTION

Various illnesses or disorders can cause muscles to contract inappropriately. Examinations such as physical exams, blood serum electrolyte studies, CAT scans, X-rays, polysomnograms with extra monitoring leads, and others, are performed in the work up of these problems. From these exams, a determination is made which muscles are the most likely to cramp. Sometimes, a patient will have recurring cramps in the same muscle group hereby obviating some examinations.

A person having night leg cramps inserts his/her leg into a stocking-like means before retiring to sleep. Strategically placed within the stocking-like means are sets of electrodes for sensing and pulsing muscles. The sensing means transmits to a monitoring means which records and sends monitored parameters to a computer controller means which is operatively attached to a pulsing lead(s). The sensing means is positioned on the muscle expected to cramp. The pulsing lead is positioned on the physiologically opposing muscle. The stocking-like means has multiple sets of leads for monitoring and pulsing. The computer is either physically attached via wires to the subject or data is passed and returned via a transmission means.

Theory of operation: [(m1) and (m2) are physiologically opposing muscles] a muscle which causes night leg cramps, for example the gastrocnemus calf muscle(m1) at the back of the leg, is monitored. As this muscle begins to cramp, the monitoring device records and sends data to a microprocessor under the control of a rule-based program, which reacts at predetermined points. On proper recognition that an inappropriate muscle(m1) contraction is about to occur, a stimulating signal is then sent to the physiologically opposing muscle(m2), in this case the pretibial muscle in the front of the leg. This stimulus causes increased tone or a contraction of the opposing muscle(m2). The body-mind is tricked into thinking a volitional movement is requested and a relaxing signal is sent through the nervous system to the physiologically opposing muscle(m1). Thus, the cramping muscle(m1) is relaxed, thereby preventing or stopping the cramp. Monitoring and pulsing occur without sleep arousal, and the subject is never aware of a cramp being aborted.

The device contains electrical circuits for processing data from the sensing/monitoring means, generating stimuli to the stimulating electrode, and timing both. Various mechanical, electrical, chemical and other biological monitoring methods commonly available in medical applications may be used. Various parameters can be set or predetermined, with pulsing stimuli having varying qualities of wave form, frequency, amplitude, voltage, or other qualities. The sensing data may be amplified and displayed on an oscilloscope or other means. The recorded data may be saved to computer or printed to paper.

It is the combination of these devices and method of relieving an inappropriate muscle contraction using the physiologic principle of muscles set in opposition which makes this invention novel.

The EX-Cramp™—a device for relieving cramping muscles has a means to monitor muscles and a means to cause a contraction of specific physiologically opposing muscle, or groups of muscle or parallel muscle, thereby inducing a relaxation within the cramping muscle thereby aborting or preventing inappropriate muscle contraction.

The EX-Cramp™—a device for relieving cramping muscles improves a user's sleep, thereby decreasing daytime sleepiness and fatigue, and resultant morbidity and mortality. It obviates the need for certain medications, physical therapy sessions, and surgical treatments.

The EX-Cramp™—a device for relieving cramping muscles may utilize any appropriate means of sensing/ monitoring including but not limited to brain waves, nerve conduction, electrical, myo-electrical, mechanical, myomechanical, and/or chemical means.

BRIEF DESCRIPTION OF DRAWINGS

FIGS. 3 and 3A schematically show brain wave monitoring.

FIGS. 1-4 schematically show composition of a controller means.

DETAILED DESCRIPTION OF THE PREFERRED EMBODIMENT

Figure 1:
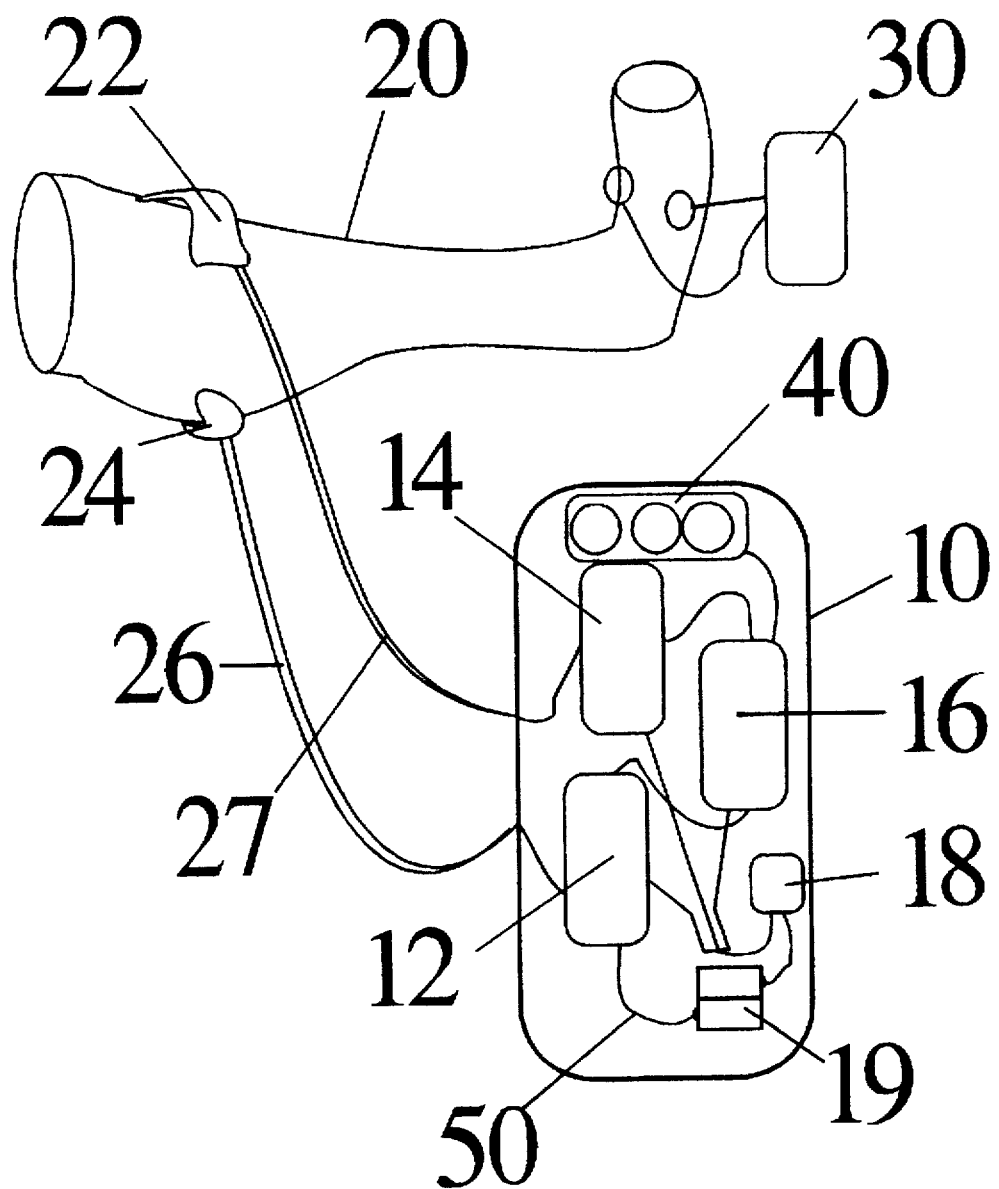
FIG. 1 is a schematic drawing of EX-Cramp™—a device for relieving cramping muscles showing stocking support means having electrodes for monitoring and pulse generating with master controller unit attached and with secondary controller unit attached distally.

The present invention is schematically represented in FIGS. 1-4 wherein as is seen in FIG. 1, a primary master unit(10) having controller means(16) to monitor(12) and stimulate(14) muscles and a positioning means(20) for securing electrodes to a skin surface.

A user who has night leg cramps, will sleep with his/her leg inserted into the stocking-like positioning means(20). On an assumption that the calf muscle, for example, at the back of leg is the night leg cramping muscle, then the sensing means(24) will be apposed to the skin overlying the calf muscle and the stimulating electrode means(22) will be apposed to the skin overlying the physiologically opposing pretibial muscle in the front of the leg. As a muscle cramp begins to occur, a signal traverses wires(26) to the monitoring means(12) whereupon circuitry means(50) within the primary master unit(10) will pass the signal to the controller means(16) thereafter the stimulating means(14) is activated to send stimulating signals through wires(27) to the stimulating electrode means(22) causing the pretibial muscle of the front of the leg to contract thereby physiologically relaxing the cramping muscle.

Figure 4:
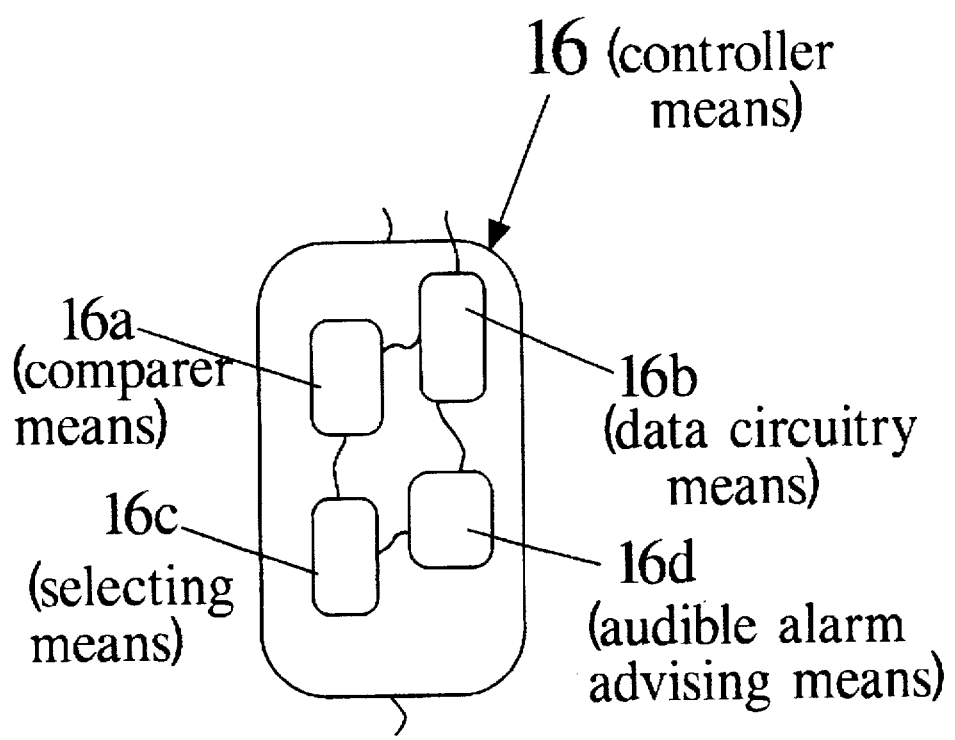

The primary master (10) unit has an rechargeable energy source(19) and a switching means(18) to turn the unit on and off, and with other circuitry having stand-by basis until needed for battery conservation. Also, within is displaying means(40) for displaying data, and chronography. The controller means(16) is schematically represented in FIG. 4, having: a comparer means(16a) for comparing sets of parameters of muscle contraction status, using said comparisons for stimulation and for modifying stimulation; a selecting means(16c) for selecting the time interval over which said monitoring means operates; an audible alarm advising means(16d) operatively connected to said sensing means for advising an operator of lead displacement and/or malfunction; and data circuitry means(16b) for sending data to the displaying means.

There can be within or external one or more secondary controller means(30) for simultaneous monitoring and stimulating.

The primary master controller means(10) has circuits incorporating incoming sensing information, comparing predetermined sets of parameters and other algorithmic determinations; circuits for controlling strength, duration, wave forms and other parameters of stimulation; and circuits for timing, synchronizing delivery of stimulation, duration, time of day and other parameters.

Various sensing means(24) of the electrical, mechanical or chemical varieties are used.

Figures 2, 2A:
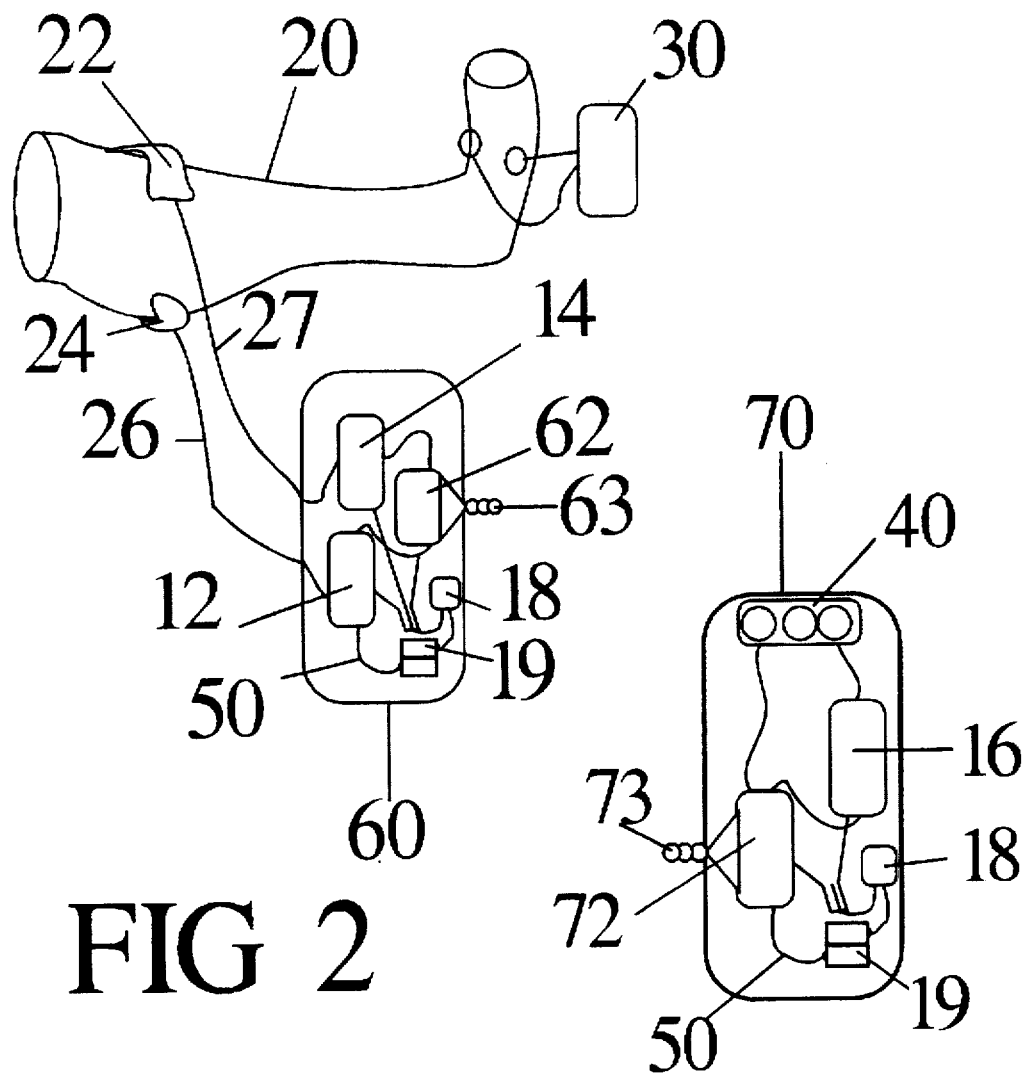
FIGS. 2 and 2A are schematic drawings of an alternative EX-Cramp™—a device for relieving cramping muscles having transmission and receiving means.

Alternatively as seen in FIGS. 2, 2A the primary master controller unit(70) is not physically attached to the subject. In this configuration, as is seen in FIG. 2, the monitoring means(12) and the stimulating means(14) are within a separate unit(60) which is placed within or near the positioning means(20) and having a transmission/receiving means(62) to transfer data. Data is transferred to the master controller unit(70) through transmission/receiving means (72). Signals are then transferred on to the pulse generator (14). The telemetry transmission means may be local within the room, or via telephone or satellite transmission to other parts of the world. Telemetry communication is preferably effected by transmission and reception, via antennae(63,73), of electromagnetic radiation modulated in accordance with the data to be sensed continuously establishing from said signals the state of contraction and simulation. More particularly, the controller means(16) is preferably adapted for comparing the sensor signals to stored threshold values which are indicative of pre-determined transition points between states of contraction, and when the received signal values correlate with stored values, then causing the stimulating means to vary parameter selection.

FIG. 3 schematically shows brain wave monitoring for cramp or sleep disorder relief, in which electrodes are typically placed around head (82,83). In this case sensing signals, traverse wires(26) to monitoring means(12) and then onto transmission antenna(63) and then, as is seen in FIG. 3A, onto antenna(73) of the primary master controller unit(70) working its way to stimulating(22) electrodes as above detailed. Transmission may occur with telemetry as above. Alternatively, a single unit may be used as in the first configuration. Also, there can be one or more secondary(30) units with other leads for synchronized monitoring and stimulation to achieve additive effects.

Although the principal application is that of assessing the status of a muscle and relieving a cramping muscle, the device has many other applications including: relieving muscle cramping at sporting events; obviating the need for general anesthesia on the occasion of positioning casts in persons afflicted with spasm disorders and others.

The foregoing description taken together with the appended claims constitute a disclosure such as to enable a person skilled in the biomedical data processing art and having the benefit of the teachings contained therein to make and use the invention. Further, the structure herein described meets the objects of invention and generally constitute a meritorious advance in the art unobvious to such a person not having the benefit of these teachings.

While the use of the EX-Cramp™—a device for relieving cramping muscles is novel, and the above description contains many specificities, these should not be considered as limitations on the scope of invention, but rather as exemplification's of preferred embodiments thereof Many other variations are possible, for example, permanently implanted monitoring and stimulating electrodes and devices can be used; or other means to support monitoring electrodes and energizing electrodes can be devised. Accordingly, the scope of the invention should be determined not by the embodiments illustrated, but by the appended claims and their legal equivalencies.

I claim:

1. An apparatus for relieving an inappropriate muscle contraction by electrically stimulating a physiologically opposing muscle comprising:

a sensing means for sensing a specific parameter of an inappropriate muscle contraction of a subject;

a monitoring means operatively associated with said sensing means for monitoring said specific parameter;

said monitoring means including a stimulating means for sending a modifiable stimulus to a physiologically opposing muscle; and said stimulating means operatively associated with and including an electrode assembly means and a positioning means for positioning said electrode assembly means on the subject against the skin overlying said opposing muscle of the subject.

2. A apparatus of claim 1 wherein said specific parameter comprises electrical muscle contraction status.

3. A apparatus of claim 1 wherein said specific parameter comprises mechanical muscle contraction status.

4. A apparatus of claim 1 wherein said specific parameter comprises nerve conduction.

5. A apparatus of claim 1 wherein said specific parameter comprises chemical muscle contraction status.

6. A apparatus of claim 1 wherein said specific parameter comprises brain activity.

7. An apparatus of claim 1 wherein said monitoring means is operatively associated with and including an energy means for providing energy, a switching means for switching said energy means on and off, and a controller means;

wherein said controller means having a comparer means for comparing sets of parameters, using said comparisons for stimulus and for modifying stimulus, a selecting means for selecting a time interval over which said monitoring means operates, a displaying means for displaying the monitored values, and an audible alarm advising means for advising of a problem with said sensing means, said monitoring means, said stimulating means, said controller means, said electrode assembly means and said positioning means.

8. An apparatus of claim 1 wherein said sensing means is adapted to sense said specific parameter prior to and after said stimulus for modifying a next stimulus.

9. An apparatus of claim 1 wherein said positioning means is adapted for attaching said sensing means and said stimulating means to generally all body parts of the subject.

10. An apparatus of claim 7 wherein said controller means is not in unity with said monitoring means and wherein a transmission/receiving means for providing data communication operatively occurs between said controller means and said monitoring means.

11. An apparatus for relieving an inappropriate muscle contraction by electrically stimulating a physiologically opposing muscle comprising: a manually positioned stimulating means comprising an electrode assembly means for placing an electrode on the subject against the skin overlying said opposing muscle of a subject; an energy means for providing energy, a switching means for switching said energy means on and off, and a stimulus controller means for controlling stimulating pulse frequency, pulse width, pulse amplitude.

12. A method for relieving an inappropriate muscle contraction by electrically stimulating a physiologically opposing muscle by monitoring and stimulating muscles wherein is included at least one unit having a means for data transmission/reception comprising the following steps:

a. modifying a positioning means for electrode placement to fit the body area being monitored and stimulated;

b. placing electrodes onto a subject's skin overlying a muscle expected to cause an inappropriate muscle cramping;

c. monitoring and sensing the muscle contraction status of a muscle;

d. placing electrodes onto the skin of its physiologic opposing muscle for stimulating the muscle at appropriate times and intervals;

e. monitoring said sensed muscle and comparing parameters monitored to predetermined parameters, and sending a stimulus to the opposing muscle causing increased muscle tension and contraction, thereby relieving or preventing an inappropriate muscle contraction of the sensed muscle;

f. optimizing stimulation (wave form, width, frequency, amplitude) by feedback of monitored muscles and responses to stimulation;

g. notifying operator by an audible alarm of malfunction of lead displacement, of arousal, or circuitry failure.

13. A method for relieving an inappropriate muscle contraction by electrically stimulating a physiologically opposing muscle by monitoring brain activity and stimulating muscles wherein is included at least one unit having a means for data transmission/reception comprising the following steps:

a. placing electrodes onto a subject's head for monitoring brain activation involved in muscle movement;

b. placing electrodes onto the skin overlying muscles for stimulating a muscle at appropriate times and intervals;

c. monitoring brain activation for inappropriate muscle contraction and comparing parameters monitored to predetermined parameters, and sending a stimulus to an expected physiologically opposing muscle increasing muscle tension and contraction, thereby relieving or preventing an inappropriate muscle contraction;

d. optimizing stimulation (wave form, width, frequency, amplitude) by feedback of monitored muscles, brain activation, and responses to stimulation;

e. notifying an operator by an audible alarm of malfunction of lead displacement, of arousal, of circuitry failure;

f. modifying a positioning means for electrode placement to fit the body area being stimulated.

14. A method for relieving an inappropriate muscle contraction by electrically stimulating a physiologically opposing muscle comprising the following steps:

a. identifying a muscle that is cramping;

b. manually placing stimulating electrodes onto the opposing muscle, turning on the energy to cause muscle tension and contraction of the opposing muscle, thereby relieving the cramp;

c. optimizing stimulation (wave form, width, frequency, amplitude) by operator.

15. A method for relieving a sleep disorder having muscle contractions by electrically stimulating a physiologically opposing muscle by monitoring brain activity and stimulating muscles wherein is included at least one unit having a means for data transmission/reception comprising the following steps:

a. placing electrodes onto a subject's head for monitoring brain activation involved in muscle movement of a sleep disorder;

b. placing electrodes onto the skin overlying muscle(s) for stimulating a muscle(s) at appropriate times and intervals;

c. monitoring brain activation and comparing parameters monitored to predetermined parameters, and sending a stimulus to an expected physiologically opposing muscle(s) to the monitored brain activation involved in muscle movement of the sleep disorder, thereby relieving or preventing an inappropriate movement within the sleep disorder;

d. optimzing stimulation (wave form, width, frequency, amplitude) by feedback of monitored muscles, brain activation, and responses to stimulation;

e. notifying an operator by an audible alarm of malfunction of lead displacement, of arousal, of circuitry failure;

f. modifying a positioning means for electrode placement to fit the body area being monitored for the sleep disorder.

* * * * *